(12) United States Patent
Carter et al.

(10) Patent No.: US 8,905,974 B2
(45) Date of Patent: Dec. 9, 2014

(54) WEARABLE INFUSION DEVICE AND SYSTEM

(71) Applicant: Calibra Medical, Inc., Redwood City, CA (US)

(72) Inventors: Brett Carter, Monroe, WA (US); John McKenzie, San Carlos, CA (US); John M. Adams, Snohomish, WA (US); Brett Cross, Seattle, WA (US); Travis Marsot, Mountain View, CA (US)

(73) Assignee: Calibra Medical, Inc., Redwood City, CA (US)

( * ) Notice: Subject to any disclaimer, the term of this patent is extended or adjusted under 35 U.S.C. 154(b) by 0 days.

(21) Appl. No.: 13/737,859

(22) Filed: Jan. 9, 2013

(65) Prior Publication Data

US 2013/0123709 A1 May 16, 2013

Related U.S. Application Data

(63) Continuation of application No. 12/616,582, filed on Nov. 11, 2009, now Pat. No. 8,449,504.

(51) Int. Cl.
*A61M 5/162* (2006.01)
*A61M 5/158* (2006.01)
*A61M 5/168* (2006.01)
*A61M 5/142* (2006.01)

(52) U.S. Cl.
CPC .............. *A61M 5/162* (2013.01); *A61M 5/158* (2013.01); *A61M 2005/14252* (2013.01); *A61M 5/16831* (2013.01); *A61M 5/14248* (2013.01); *A61M 5/14244* (2013.01); *A61M 5/1626* (2013.01); *A61M 2005/1585* (2013.01)
USPC ........................ 604/180; 604/164.01; 604/174

(58) Field of Classification Search
CPC . A61M 5/162; A61M 25/02; A61M 5/14248; A61M 2005/1585; A61M 2005/14252; A61M 5/14244; A61M 5/16831; A61M 5/158
USPC ................... 604/180, 181, 192, 389, 164.01, 604/171–174
See application file for complete search history.

(56) References Cited

U.S. PATENT DOCUMENTS

| | | | |
|---|---|---|---|
| 4,755,173 A | 7/1988 | Konopka et al. | |
| 6,685,674 B2 | 2/2004 | Douglas et al. | |

(Continued)

FOREIGN PATENT DOCUMENTS

WO  WO 2010/051079 A3  5/2010

OTHER PUBLICATIONS

PCT International Search Report and Written Opinion for PCT Application No. PCT/US2010/056715; Aug. 25, 2011.

*Primary Examiner* — Nicholas Lucchesi
*Assistant Examiner* — Gerald Landry, II

(57) ABSTRACT

Disclosed is a drug infusion system comprising a drug infusion device having a reservoir, a window for viewing the contents of the reservoir, a cannula arranged to be deployed beneath the skin of a patient, and an actuator configured to be manually actuated to drive a medicament from the reservoir to the cannula. The system also has a cannula cover and a needle handle that holds a needle for insertion into the patient. The cannula cover and needle handle are detachably attached to the drug infusion device, and each is attachable to the other. The device further comprises a septum and a septum pincher to seal the device. The device also comprises a pumping mechanism, part of which are a last-dose lock-out mechanism and an occlusion detection mechanism, both of which operate on the same actuator.

1 Claim, 13 Drawing Sheets

(56) References Cited

U.S. PATENT DOCUMENTS

| | | |
|---|---|---|
| 6,786,244 B1 | 9/2004 | Jones |
| 2002/0177809 A1* | 11/2002 | Kriesel et al. ............ 604/132 |
| 2004/0158207 A1 | 8/2004 | Hunn et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2007/0299408 A1* | 12/2007 | Alferness et al. ......... 604/250 |
| 2008/0021375 A1* | 1/2008 | Burns et al. .............. 604/27 |
| 2008/0119790 A1* | 5/2008 | Hawkins et al. .......... 604/131 |
| 2008/0269683 A1* | 10/2008 | Bikovsky ............... 604/164.12 |
| 2008/0281270 A1 | 11/2008 | Cross et al. |
| 2008/0287869 A1* | 11/2008 | Chun ....................... 604/110 |
| 2009/0012473 A1 | 1/2009 | Stettler et al. |
| 2009/0054866 A1* | 2/2009 | Teisen-Simony et al. .... 604/506 |
| 2009/0088690 A1 | 4/2009 | Carter et al. |
| 2009/0088694 A1 | 4/2009 | Carter et al. |
| 2009/0259182 A1 | 10/2009 | Cross et al. |
| 2009/0281525 A1* | 11/2009 | Harding et al. ........... 604/537 |
| 2010/0049128 A1* | 2/2010 | McKenzie et al. ......... 604/135 |
| 2010/0137695 A1* | 6/2010 | Yodfat et al. ............. 600/345 |
| 2010/0152666 A1 | 6/2010 | Carter et al. |
| 2010/0243099 A1 | 9/2010 | Yodfat |
| 2010/0286602 A1 | 11/2010 | Carter et al. |
| 2012/0238962 A1 | 9/2012 | Chin et al. |
| 2012/0245558 A1* | 9/2012 | Durack et al. ............ 604/506 |

\* cited by examiner

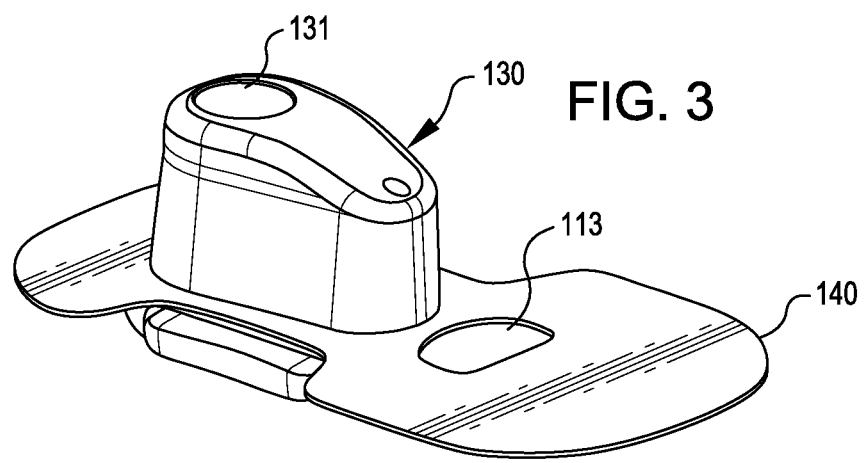
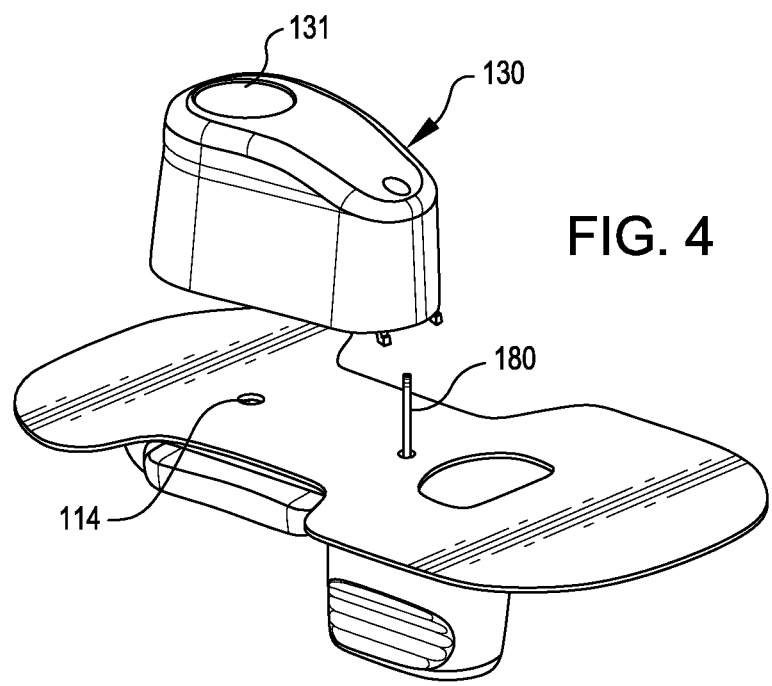

WEARABLE INFUSION DEVICE AND SYSTEM

CROSS-REFERENCE

This application is a continuation application which claims the benefits of pending U.S. patent application Ser. No. 12/616,582, filed on Nov. 11, 2009, the entirety of which prior application is incorporated herein by reference.

FIELD OF THE INVENTION

The present invention relates to infusion devices and more particularly to such devices that enable liquid medicaments to be conveniently and safely self-administered by a patient.

BACKGROUND OF THE INVENTION

Administration of insulin has traditionally been accomplished using a syringe. Recently, needle carrying pen-like devices have also been employed for this purpose. Both forms of insulin administration require the patients to stick themselves each time they inject insulin, often many times a day. Thus, these traditional forms of insulin administration have been a rather pervasive intrusion in the lives and routines of the patients who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use. Great care in programming the devices is required because the pumps generally carry sufficient insulin to last a few days. Improper programming or general operation of the pumps can result in delivery of an excessive amount of insulin which can be very dangerous and even fatal.

Many patients are also reluctant to wear a pump device because they can be socially awkward. The devices are generally quite noticeable and can be as large as a pager. Adding to their awkwardness is their attachment to the outside of the patient's clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. The device may be attached to the patient under the patient's clothing to deliver insulin into the patient by the manual pumping of small doses of insulin out the distal end of a temporarily in-dwelling cannula that is made a part of the pump device. The cannula may be made a part of the drug delivery device before, during or after the attachment of the drug delivery device to the skin of the patient. The device may be made quite small and, when worn under the clothes, entirely unnoticeable in most social situations. It may still carry sufficient insulin to provide the patient the necessary dose for several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference is made to co-pending application Ser. No. 11/906,130, filed on Sep. 28, 2007 with the title DISPOSABLE INFUSION DEVICE WITH DUAL VALVE SYSTEM, which application is owned by the assignee of this application and hereby incorporated herein by reference in its entirety.

The present invention provides further improvement to the devices disclosed in the above referenced co-pending application. More particularly, the devices disclosed herein provide for improved patient safety and/or convenience. For example, embodiments of the invention described here provide, improved sealing of the medicament, more convenient cannula deployment, device misuse prevention, easier priming methods, and fluid path occlusion detection. These and other advantages are addressed herein.

SUMMARY OF THE INVENTION

According to one embodiment, a drug infusion system comprises a skin-adherable drug infusion device comprising a reservoir, a cannula arranged to be deployed beneath the skin of a patient, and an actuator configured to be manually actuated to drive a medicament from the reservoir to the cannula. The system further comprises a cannula cover and a needle handle. The needle handle holds a needle for insertion into the patient.

The cannula cover may be configured to be detachably attached to the drug infusion device. The needle handle may be configured to be detachably attached to the drug infusion device.

The needle handle may be configured to be coupled to the cannula cover. The cannula cover may include a cavity for receiving the needle when the needle handle is coupled to the cannula cover.

The device preferably includes an adhesive layer for adhering to the skin of a user and a removable cover overlying the adhesive layer. The cannula cover may be attached to the removable cover on the adhesive layer so that as the cannula cover is removed from the device, the removable cover is also removed with it.

The device may comprise a last-dose lock-out mechanism and/or an occlusion detection mechanism. Both the last-dose lock-out mechanism and the occlusion detection mechanism may be configured to operate on the same actuator.

The system may further comprise an inserter for inserting the needle into the skin of a patient. The device may include a fill port through which the reservoir receives medicament. The cannula cover may include a guide port that guides a medicament supply instrument into alignment with the fill port. The guide port may include a stop structure that limits penetration of the medicament supply instrument within the fill port. The cannula cover may include a priming window through which priming of the device may be observed. The device may include a window for viewing the contents of the reservoir.

According to another embodiment, a drug infusion device comprises a skin-adherable surface, a reservoir for holding a medicament, a cannula arranged to be deployed beneath the skin of a patient that delivers the medicament to the patient, an actuator to drive a medicament from the reservoir to the cannula, an insertion needle port that receives an insertion needle and which fluidly communicates with the cannula, a septum configured to seal the insertion needle port, and a septum pincher configured to press against the septum to assist the septum in sealing the insertion needle port.

According to a further embodiment, a drug infusion system comprises a skin-adherable drug infusion device comprising a reservoir, a cannula arranged to be deployed beneath the skin of a patient, and an actuator configured to be manually actuated to drive a medicament from the reservoir to the cannula. The system further comprises a cannula cover arranged to be releasably joined with the device to protect the cannula and is arranged to capture medicament during priming of the device.

The channel may include a plurality of inwardly radially projecting fins for capturing the medicament during priming of the device. The fins are preferably longitudinally extending within the channel. The cannula cover may include a priming window through which priming of the device may be observed within the channel.

According to a still further embodiment, a drug infusion device comprises a skin-adherable surface, a reservoir for holding a medicament, a cannula arranged to be deployed beneath the skin of a patient that delivers the medicament to the patient, and an actuator to drive a medicament from the reservoir to the cannula. The cannula includes a tip end output port and at least one side output port. The cannula may include a pair of side output ports. The side output ports may be directly opposite each other.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 3 is a view of the bottom of the drug infusion system of FIG. 1;

FIG. 4 is an exploded view in perspective of the drug infusion system of FIG. 3;

DETAILED DESCRIPTION

The present invention is generally directed to infusion devices as, for example, where each manual actuation of the device by a patient administers a preset dose of a medicament (such as insulin). In exemplary embodiments, the device is filled with a predetermined volume of insulin and then worn on the skin for a period of time (e.g., up to three days). Whenever a dose of medicament is desired, the device is manually actuated (or activated) to provide a dose of medicament to the patient.

Figure 1:
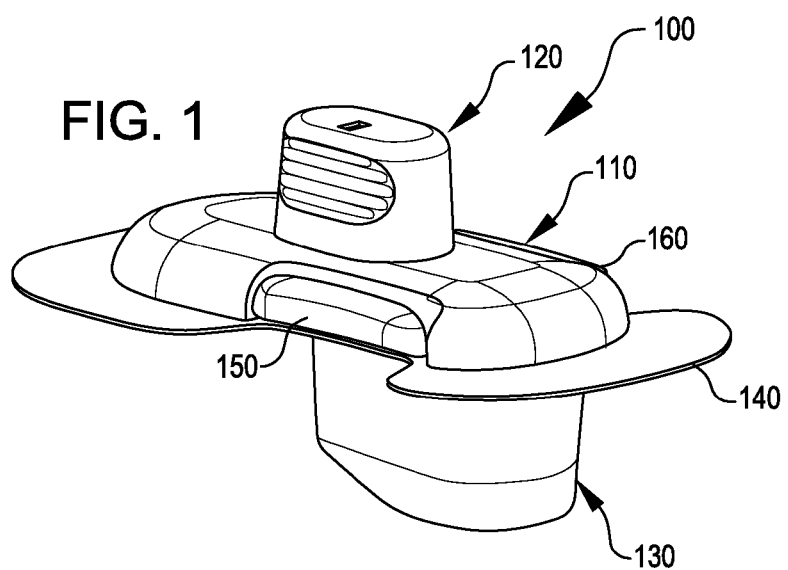
FIG. 1a is a top perspective view of a drug infusion system according to an embodiment of the present invention.
Figure 2:
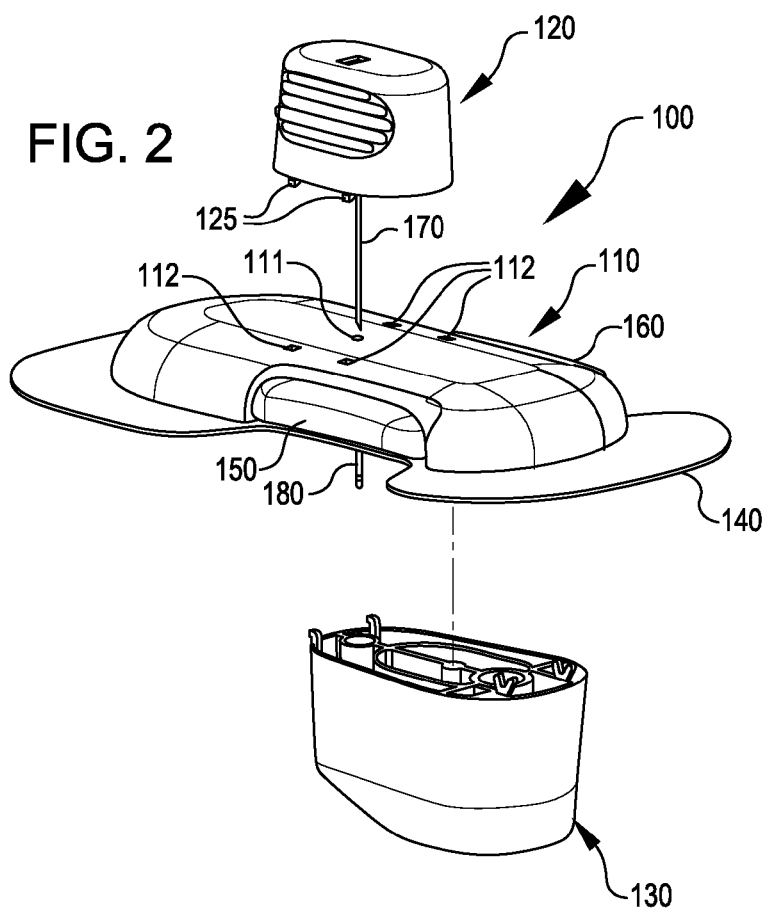
FIG. 2 is an exploded view in perspective of the infusion system of FIG. 2.

FIGS. 1 and 2 show an infusion system 100 embodying the present invention. The system 100 comprises an infusion device 110, a needle handle 120 which carries an insertion needle and a syringe guide and cannula cover 130 (hereinafter referred to as a cannula cover) which covers a cannula 180 (180 doesn't show up until FIG. 4) that protrudes from the device. The device 110 further comprises an adhesive layer 140 on the underside of the device and actuators 150 and 160 on either side of the device. As shown in FIG. 2, the outer shell of device 110 has a needle opening 111 to receive a needle 170 which is held by the needle handle 120. The outer shell of device 110 also has notches 112 to receive corresponding latching feet 125 of the needle handle 120. The feet 125 and notches 112 permit the needle handle to be releasably joined to the device 110.

As shown in FIG. 3, adhesive layer 140, viewing window 113, and cannula cover 130 are located on the underside of device 110. Adhesive layer 140 is configured to be attached to the patient's skin and comprises a cover (not shown) that is removable for adhering to a patient's skin. Although the viewing window 113 is shown as being located on the underside of the device, it may alternatively be located on the top of the device. The window 113 is a clear portion that enables a user to look into the device and into the contents of a reservoir held within the device. It is used to visually determine the fill-level of the reservoir, to visually assist in the removal of air bubbles before cannula deployment, and optionally to notice any irregularities of the medicament within the reservoir.

The cannula cover 130 comprises an opening 131 that is configured to receive a syringe and syringe needle. Optionally, opening 131 is covered by a cover (not shown) that may be opened or removed. As will be subsequently shown in further detail, a syringe filled with medicament is inserted into opening 131. Opening 131 ultimately communicates with the reservoir within the device through a port within the device and a septum. This permits medicament to be introduced into the reservoir of device 110 for filling.

The cannula cover 130 serves a dual function. It facilitates guided coupling of the syringe to the device and provides a protective cover for the cannula. This is seen in FIG. 4. FIG. 4 shows the underside of the device that lies beneath the elevated cannula cover 130. Port 114 is in line with opening 131. This permits the syringe that enters through opening 131 to ultimately enter port 114.

Figure 5:
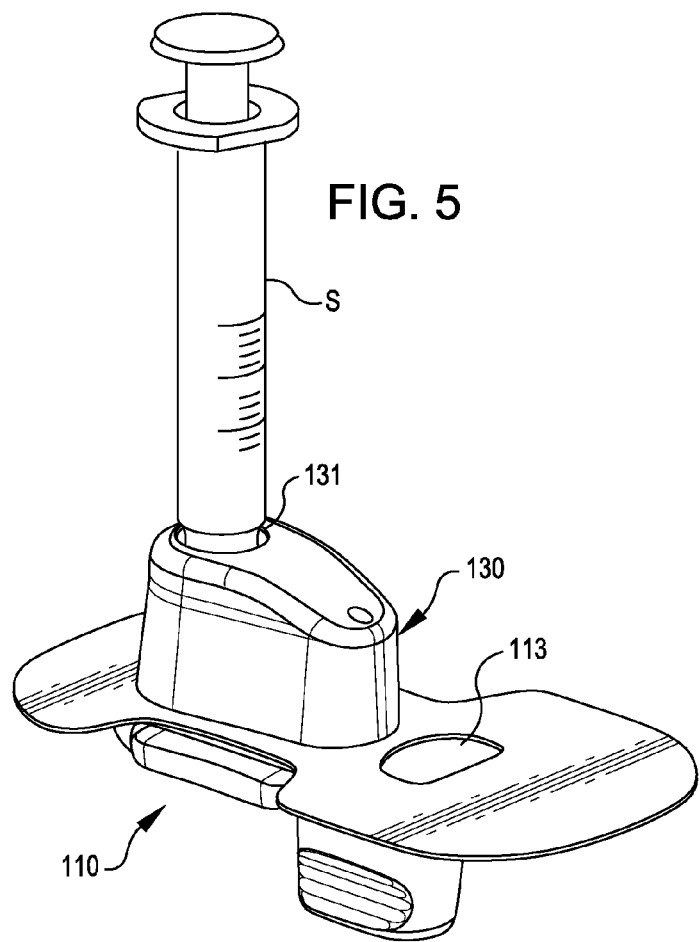
FIG. 5 is a perspective view illustrating a manner of the device of the drug infusion system of FIG. 1 according to an embodiment of the invention.
Figure 6:
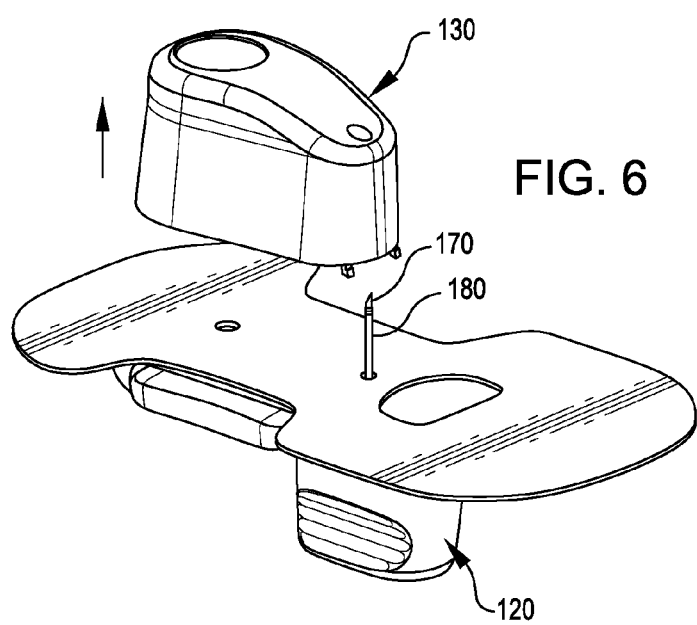
FIG. 6 is a view, similar to FIG. 4, illustrating the removal of a cannula cover of the drug infusion system of FIG. 1 according to this embodiment.

FIG. 5 illustrates the filling of the device 110. Syringe S is inserted into the port 131 of the cannula cover 130, as shown. The syringe S is used to fill the reservoir of the device with a desired quantity of the medicament. The filling of the reservoir may be observed through the viewing window 113.

Once the reservoir is filled, the cannula cover 130 is removed from the device as shown in FIG. 2b to expose the cannula 180. Protruding from the cannula 180 is the insertion needle 170. The other end of the needle 170 which is attached to the needle handle 120 on the opposite side of the device.

Prior to the placement of the device on the skin, and either prior to the removal of the syringe guide, or even just after it, the device is primed for use. Priming occurs through activating the actuator buttons to advance the fluid within the device. Fluid is directed at least partly towards the mouth of cannula 180, with the needle 170 within cannula 180.

Figure 7:
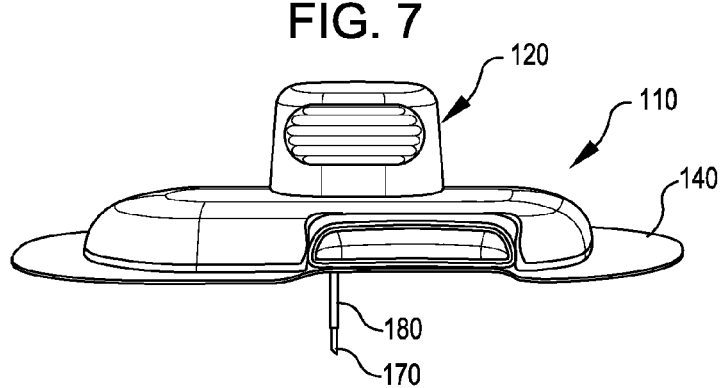
FIG. 7 is a side perspective view, illustrating the device of the drug infusion system of FIG. 1 after deployment on a user's skin.

The adhesive layer 140 is also prepared for adhesion to the skin, for example by removing a cover that overlies the adhesive. To this end, and in accordance with one embodiment of the invention, the cannula cover 130 may be attached to the cover overlying the adhesive layer of the device, such that when the cannula cover 130 is removed, the cover is also removed. The device thus prepared is then driven into the skin, as shown in FIG. 7, either by a patient pressing the device onto the skin such that the cannula 180 and the insertion needle 170 pierce the skin, or through the aid of an inserter, such as that described below and as disclosed in co-pending U.S. application Ser. No. 12/543,352, which is incorporated herein by reference. The inserter may be configured to receive device 100, or a portion thereof. Upon actuation by the patient, the inserter would drive the cannula and insertion needle into the skin of the patient.

Figure 8:
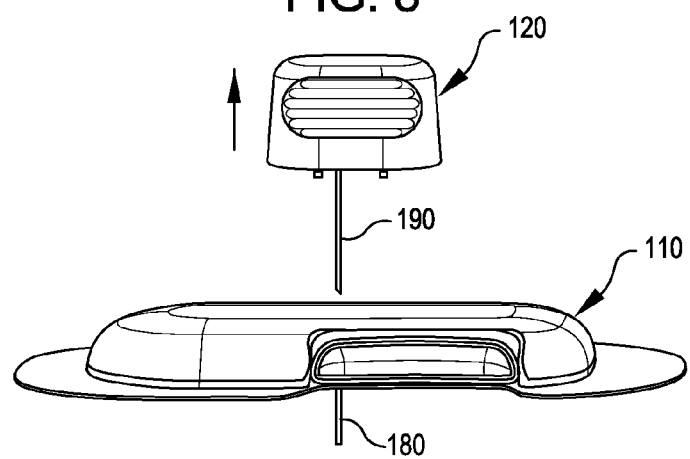
FIG. 8 is a side perspective view, illustrating the device of the drug infusion system of FIG. 1 after deployment on a user's skin and during removal of a needle and needle handle according to this embodiment.
Figure 9:
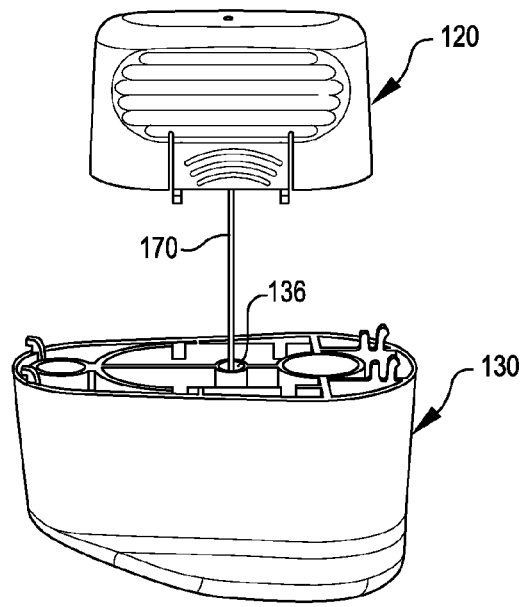
FIG. 9 is a side perspective view illustrating the safe storage of the needle in the cannula cover according to this embodiment.

Once the device is deployed on the skin, the needle handle 120 is detached from the rest of the device. This is shown in FIG. 8. Needle 170 is attached to the needle handle 120 and thus is also removed with the handle 120 from the device 110. Cannula 180 remains attached to the device 110 and thus remains within the tissue of the patient. To safely dispose of the insertion needle 170, needle handle 120 may be attached to cannula cover 130 as shown in FIG. 9. As shown here, the needle 170 is received by an elongated cavity 136 of the cannula cover 130.

Figure 10:
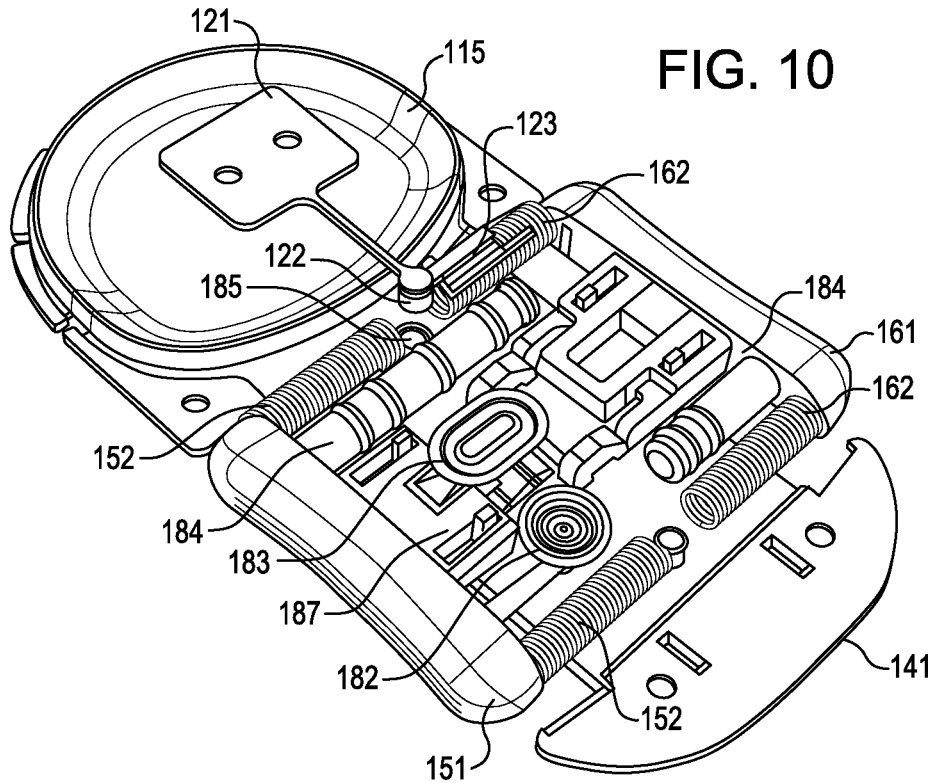
FIG. 10 is a perspective view of the device of the system of FIG. 1 with a top cover removed to illustrate the internal components of the device according to an embodiment of the invention.

Turning now to the internal components of the device 110, FIG. 10 shows the inside of device 110 from a top perspective view, with the top cover 110 removed. The device 100 comprises a reservoir 115, a needle hole cover 121, a needle septum 122, a septum pincher 123, actuator buttons 151 and 161, actuation springs 152 and 162, a base plate 141, an introducer septum 116 (which underlies port 114 in FIG. 4), pump mechanism 181, a valve stem 184, a locking mechanism 187 and a cannula port 185.

The reservoir 115 comprises a hollow base overlayed with one or more layers of flexible, bio-compatible film. The film is a laminate film of sufficient thickness and flexibility to hold a medicament. The film may be in the form of a fillable bag or pouch that is overlaid on the base, or it may be in the form of a flexible cover for the base, with the medicament directly introduced between the film and the base.

The reservoir is in communication with the introducer septum 116. Introducer septum 116 underlies port 114 (FIG. 4), and thus is the entry point for the medicament that is introduced by the syringe. Port 114 is thus in fluid communication with reservoir 115, such that medicament entering through port 114 and septum 116 is ultimately transported into reservoir 115 for storage and later delivery to cannula port 185.

In accordance with this embodiment, actuation occurs by concurrent manual depression of the actuator buttons 151 and 161. Such actuation causes the medicament to flow through the pump mechanism 181 and valve stem 184 and ultimately through the cannula and into the patient.

Figure 11:
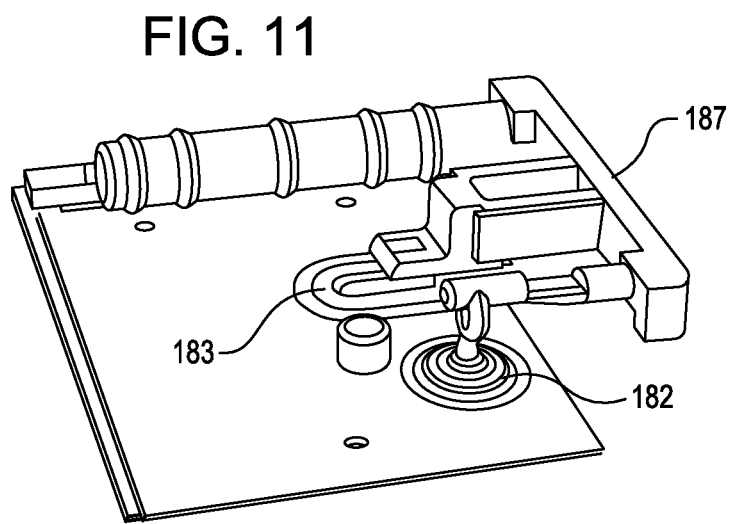
FIG. 11 is a partial perspective view illustrating the last-dose lock-out and occlusion detection mechanisms of the device according to an embodiment of the present invention.

The pump mechanism within the device is similar to that described in co-pending applications US20090088690, PCT/US2009/048922, and U.S. application Ser. No. 12/543,352. The pump mechanism is configured to be acted upon by the actuator buttons, such that when a user manually actuates the actuators, the forward actuation stroke propels medicament from the pump mechanism into the cannula. The return actuation stroke then pulls medicament from the reservoir into the pump mechanism for delivery upon the next actuation. Among other features, the pump mechanism optionally comprises a last-dose lock-out mechanism 182, similar to what was described in co-pending application US20090088690. Briefly, this last-dose lock-out mechanism 182 (shown in FIG. 11) mechanically detects the absence of medicament flowing from the reservoir to the pump mechanism. When such absence of flow occurs, the mechanism engages a portion of the locking mechanism 187. Locking mechanism 187 is connected to actuator button 151, and when engaged by the last dose lock-out mechanism 182, prevents actuator button 151 from being actuated.

The pump mechanism also optionally comprises an occlusion detection mechanism 183, similar to that described in co-pending application PCT/US2009/048922. Briefly, the occlusion detection mechanism (also shown in FIG. 11) mechanically detects an occlusion (e.g., crystallized medicament), within the medicament stream flowing through the pump mechanism 181. Once an occlusion is detected, the mechanism engages a portion of locking mechanism 187. This in turn engages a portion of actuator button 151, preventing actuator button 151 from being actuated. It should be noted that in accordance with the present invention, both the occlusion detection mechanism 183 and the last-dose lockout mechanism 182 of the device are configured to operate upon the same actuation button, providing added manufacturing efficiency and attendant cost benefits.

Figure 12:
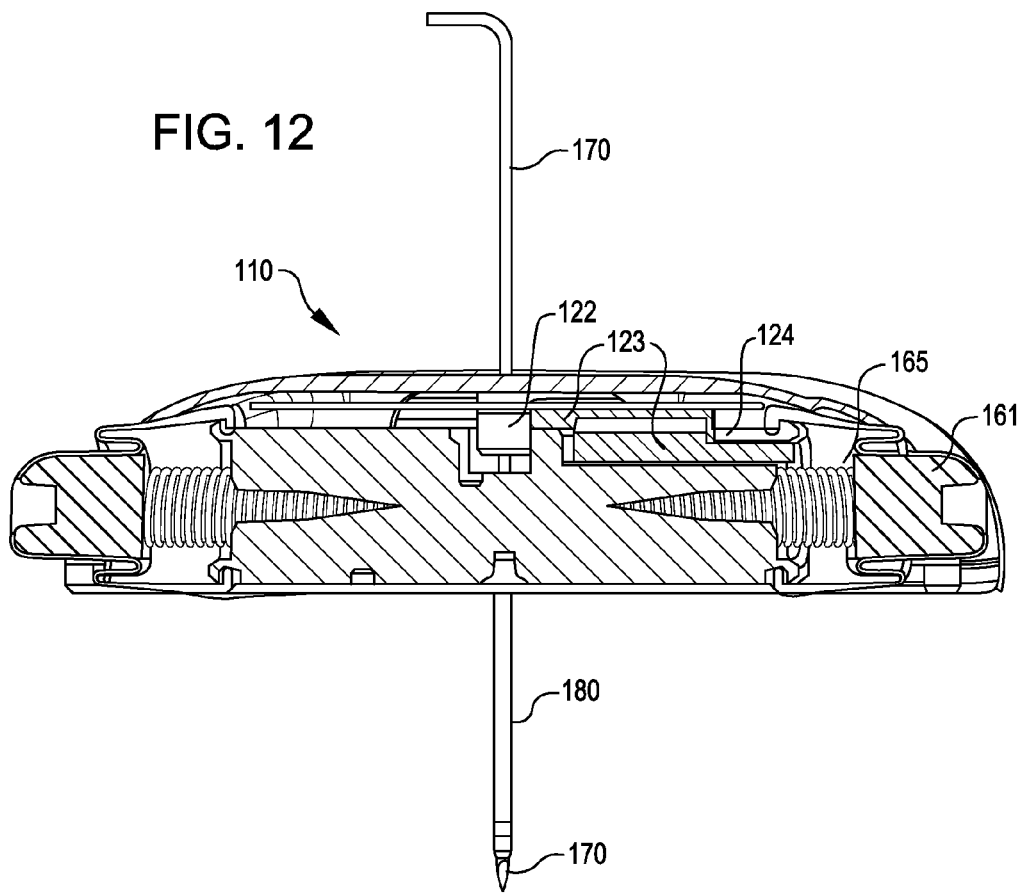
FIG. 12 is a sectional view of the device of the system of FIG. 1 illustrating internal components of the device according to this embodiment.
Figure 13:
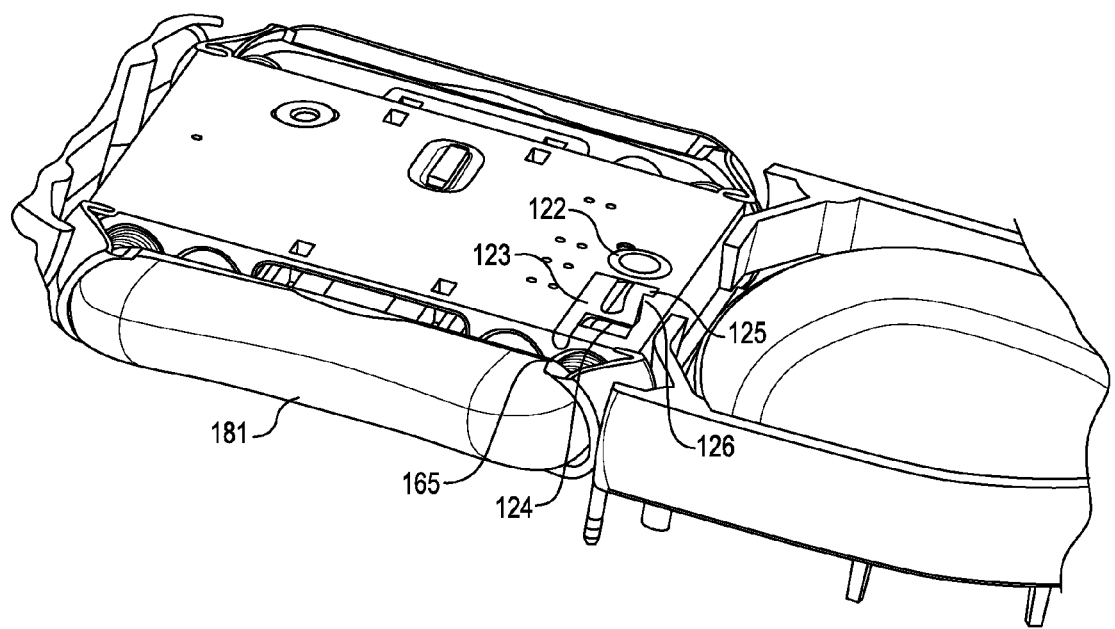
FIG. 13 is a perspective view to an enlarged scale showing of the top of the device with the cover removed to illustrate further details of the device according to this embodiment.

The device also comprises several novel safety features. One of these features is the closable needle septum, shown in FIG. 12. As previously mentioned, the needle 170 is placed through the device to extend through and out the cannula on the other side. After serving the purpose during device deployment of piercing the skin, the needle is withdrawn. In order to maintain the sterility and integrity of the internal fluid pathway of the device, a needle septum 122 is located on the inside of the device, just inside the top cover of device 110. Needle septum 122 is configured to be a self sealing septum and thus prevents any further materials from entering the device after the needle has been withdrawn. However, in some situations, after the needle is withdrawn from septum 122, it may leave a hole within septum 122. In order to close the hole, and prevent seepage of medicament into the rest of the device, a septum pincher 123 is provided and configured to press the septum closed during actuation. As can be seen in FIG. 12, which is a sectional view of the device and FIG. 13 which is a perspective view of the device, pincher 123 is slidable within a cavity 124 within the device. Pincher 123, as shown in this embodiment, has a non-uniform cross-section along all axis. However, other configurations of a pincher may be utilized. Pincher 123 is configured to be acted upon by portion 165 of actuator 161. Actuator 161 being depressed causes the pincher 123 to slide along cavity 124 and to contact and press against septum 122. This pressing of septum 122 causes it to collapse around the opening left by the needle. In one embodiment, after actuation, when the actuator button 161 returns to its normal position, the pincher 123 also slides back to its original position within cavity 124. Alternatively, as seen in FIG. 13, the pincher may be configured to permanently press against the septum upon a first actuation. To this end, pincher 123 is provided with a latching portion 125 that corresponds to a latch-receiving portion 126 in the wall of cavity 124. In this configuration, once the actuator 161 is depressed, and the pincher 123 slides forward in cavity 124, latching portion 125 slides into receiving portion 126.

Figure 14:
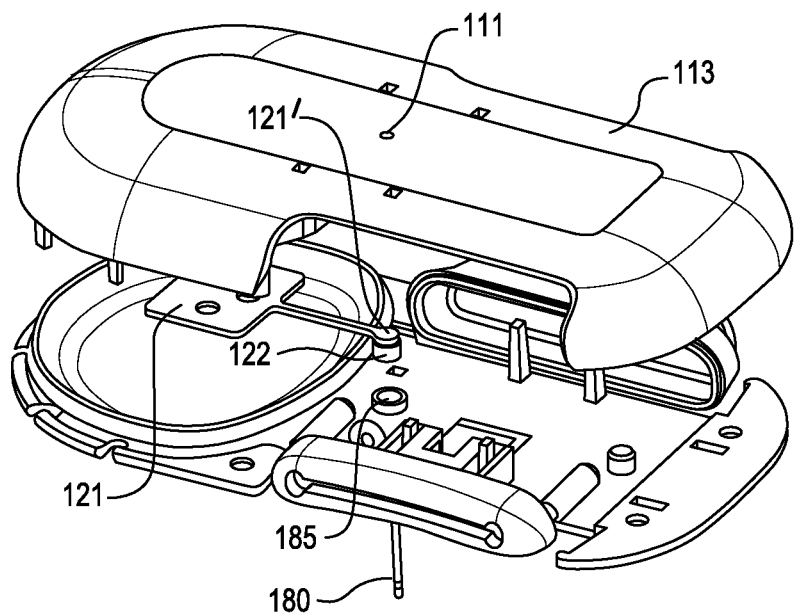
FIG. 14 is an exploded perspective view of the device illustrating selected ones of the internal components of the device.

Another safety feature is a cover for the needle hole 111. The exploded view of FIG. 14, the needle hole 111 within the top cover 113 overlies needle septum 122, which in turn overlies cannula port 185. Thus, the entry of any fluid or extraneous matter through needle hole 111 may go through cannula port 185, into cannula 180, and ultimately into the patient. This is particularly dangerous if a patient mistakenly tries to refill the reservoir of the device by inserting a syringe into the needle hole 111 and depositing a large volume of medicament therein. To prevent this scenario, a needle hole cover 121 is provided. Needle hole cover 121 is located among the internal components of the device. It is affixed to the underside of the top cover 113 of the device, and a portion of 121' covers needle septum 122. In its initial state, when the needle is pierced through the septum (not shown), the portion 121' is displaced to one side. After the needle has been removed, the portion 121' moves to cover the septum and prevent a user from accidentally or intentionally injecting any substance (including any more medicament) directly into the cannula.

Figure 15:
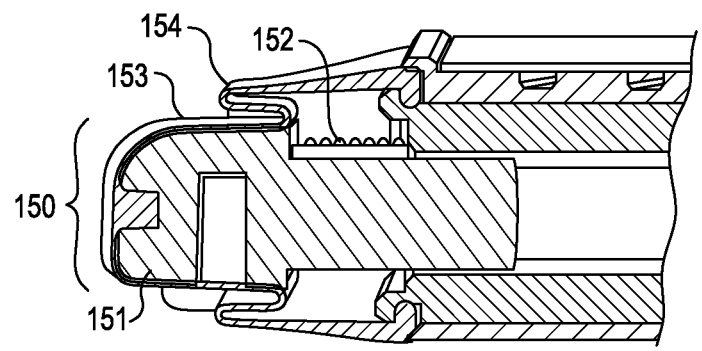
FIG. 15 is a partial, sectional side view of the device of the system of FIG. 1 to an enlarged scale illustrating an actuator of the device according to this embodiment.

Another safety feature is the prevention of extraneous materials (e.g., water, dust particles) from entering the interior of the device past the actuator elements of the device. One such provision is shown in FIG. 15. This figure exemplarily shows a detailed view of actuator 150, but it must be understood that actuator 160 may comprise similar structure and features. The actuator 150 comprises an actuator button 151 and at least one spring 152. Overlying the actuator button 151 and spring 152 is an actuator cover 153. Actuator cover overlies both button 151 and spring 152 in a manner as to prevent the entry of extraneous material into the spring components and the internal mechanisms of the device 110. Actuator cover 153 is made of a compressible substance and comprises a furrow 154. Furrow 154 comprises an undulatable fold that allows the button to be depressed and retracted while maintaining the seal that the cover 153 provides to the outside of the device.

Figure 16:
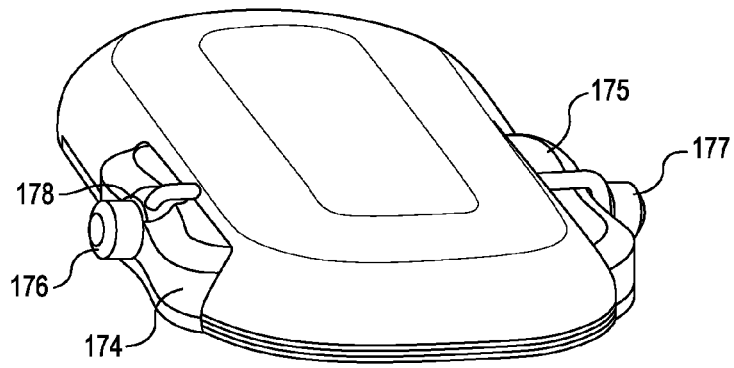
FIG. 16 is a perspective view of another device having sealed actuators in accordance with a further embodiment.
Figure 17:
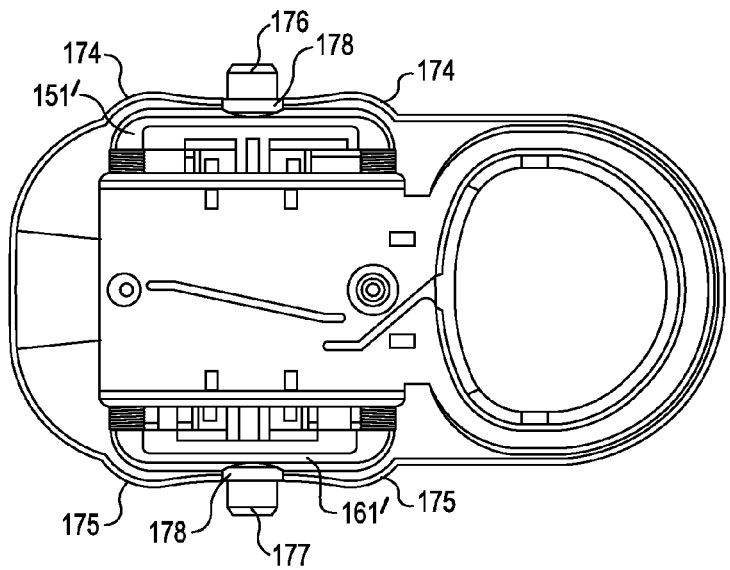
FIG. 17 is a top view of the device of FIG. 16 with portions removed to illustrate details of the actuator of the device.

Another configuration of the actuators is shown in FIGS. 16 and 17. In this embodiment, the actuator buttons 151' and 161', are overlain by casings 174 and 175 respectively. At the center of the casings, are actuator depressor buttons 176 and 177. As seen in FIG. 17, depressor buttons 176 and 177 are in mechanical communication with actuator buttons 151' and 161' respectively. When depressor button 176 is depressed, it contacts and consequently depresses actuator button 151'. Similarly, when depressor button 177 is depressed, it contacts and consequently depresses actuator button 161'. The device is thus actuated upon depression of the depressor buttons. A seal 178 may be provided around the depressor buttons, between the button and the casing, to further protect the integrity of the internal components of the device and prevent extraneous materials from entering into the device. The seal is in the form of an o-ring but may be any suitable seal.

Figure 18:
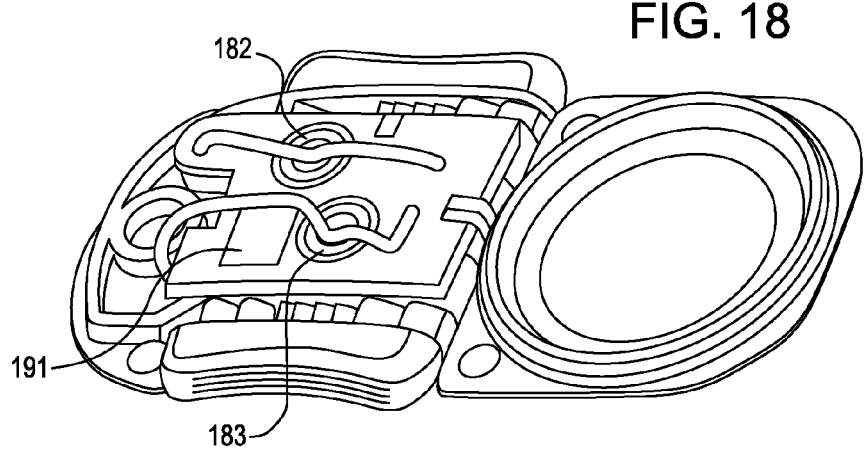
FIG. 18 is a perspective view of a drug infusion device including a filter in accordance with an embodiment that may be employed to advantage in either the device of FIG. 1 or FIG. 16.

Another feature can be provided in the form of a filter that captures any microbes or particles in the fluid stream between the reservoir and the cannula. One such filter embodying the invention is shown in FIG. 18, where filter 191 is placed within the fluid stream between the reservoir and the cannula. The filter 191 is placed in the stream between the occlusion detection mechanism 182 and the cannula. However, it may be placed anywhere along the fluid path where it is suitable. For example, if the downstream placed filter is found to interfere with the functioning of the occlusion detection mechanism 183, the filter may be placed upstream from the occlusion detection mechanism 183.

Figure 19:
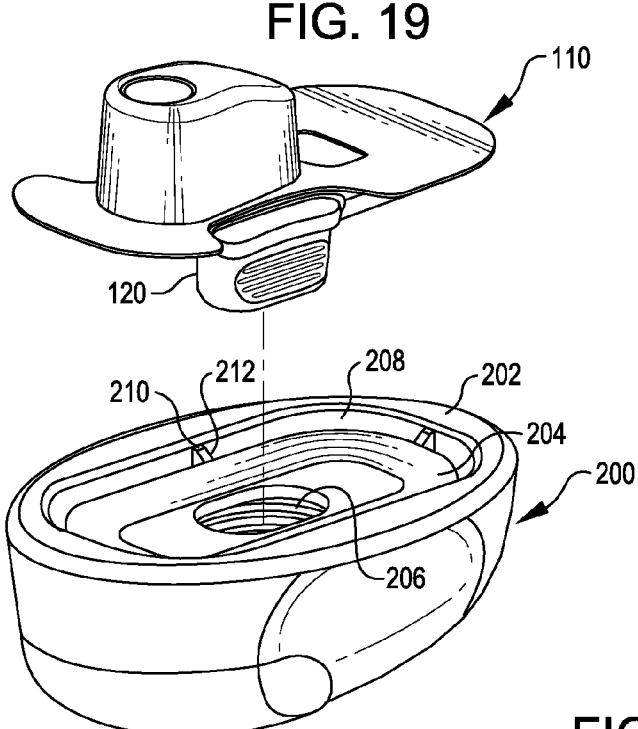
FIG. 19 is an exploded perspective view of a drug infusion device embodying the invention together with an inserter for deploying the device in accordance with further aspects of the invention.

As previously noted, the embodiments of the drug delivery device may be used in conjunction with an inserter configured to insert the needle 170 into the skin. FIG. 19 is an exploded view of the infusion device 110 and an inserter 200 for deploying the device in accordance with further aspects of the present invention. The inserter 200 includes a housing 202 dimensioned to receive the device 110. The device 110 may thus be placed into the inserter 200 in the direction of the arrow. The inserter housing 202 includes a moveable top 204 that has an inner surface contour that matches the general surface contour of the device 110. The top 204 has an opening 206 for receiving the insertion needle handle 120 that protrudes from the device 110. The inserter housing 202 has a side wall 208 that includes guide channels 210. The guide channels 210 slidingly receive guide extensions 212 that extend from the inserter top 204. The guide channels 210 and guide extensions 212 serve to controllably guide the translation of the top 204, and hence the device 110, during deployment of the device 110. To that end, the top may be manually driven by the user or the top may be driven by a mechanical drive force as may be provided by the stored energy of a drive spring (not shown) within the inserter housing 202, for example.

Figure 20:
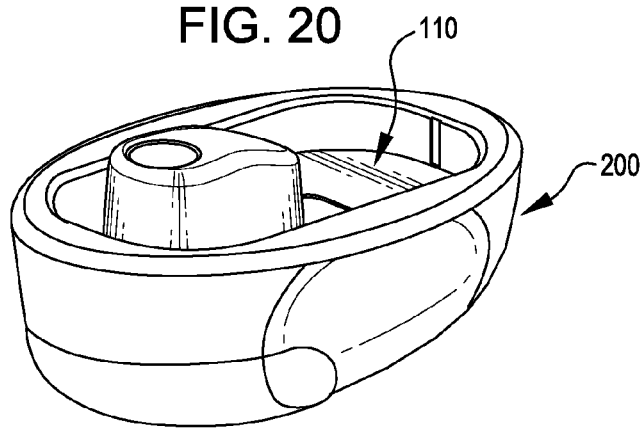
FIG. 20 is a perspective view of the device being placed into the inserter to ready deployment of the device.

As the infusion device 110 is being loaded into the inserter 200, the device 110 is pushed down into the movable top 204 of the inserter 200. As it is being pushed, the movable top 204 slides down along guide channels 210. The pushing of the movable top also compresses a spring (not shown) held under the movable top 204. At the end of the guide channels, a locking mechanism (not shown) locks the movable top in its depressed state. FIG. 20 shows the device 110 fully loaded into the inserter 200.

Figure 21:
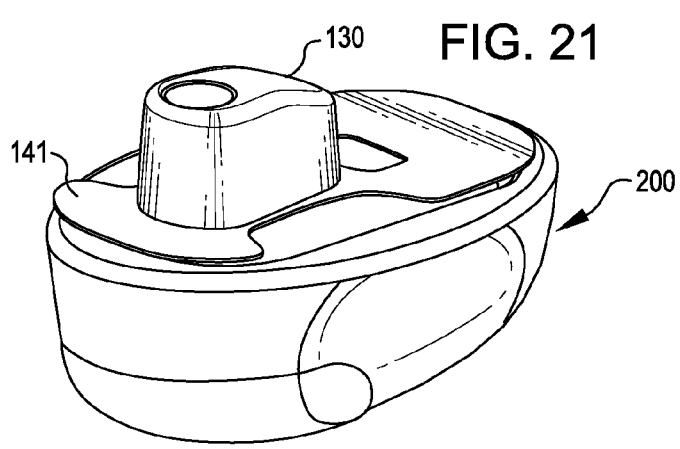
FIG. 21 is a perspective view of the device within the inserter.

Now, the cannula cover 130 may be removed from the device 110. FIG. 21 shows a removable cover 141 that covered the adhesive layer 140 (FIG. 1) being removed along with the cannula cover 130. To that end, the cannula cover 130 may be releasably adhered to the cover 141 to permit the cover 141 to be removed with the cannula cover 130 but also later separated there from. The device 110 is now ready for deployment. If the removable cover 141 is not attached to the cannula cover 130, it is removed from the device 110 at this time and the device 110 will now be ready for deployment with the inserter 200.

Figure 22:
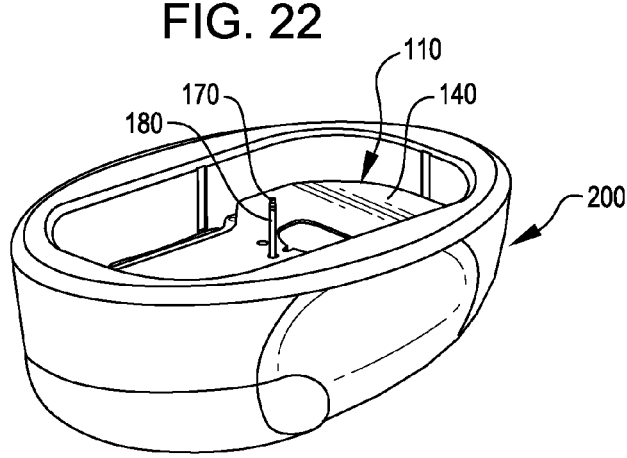
FIG. 22 is a perspective view of the device within the inserter and after the cannula cover has been removed.
Figure 23:
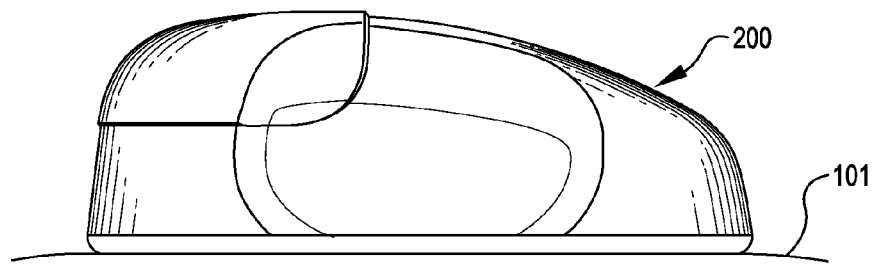
FIG. 23 is a side view of the inserter placed against a user's skin just prior to deployment of the device within the inserter.

FIG. 22 shows the device 110 and the inserter 200 after the cannula cover and removable cover have been removed. This leaves the cannula 180 and the insertion needle exposed to penetrate the user's skin and the adhesive layer 140 ready for attaching the device 110 to the user's skin. FIG. 23 shows that the inserter 200 has been placed against the skin 101 of the patient. Now, upon actuation of the inserter 200, either by manual force or released stored force from the internal spring, the entire device 100 will be driven to the skin of the patient. This will cause the cannula and insertion needle to penetrate the patient's skin and the adhesive surface of the base of the device to contact and be adhered to the patient's skin.

Figure 24:
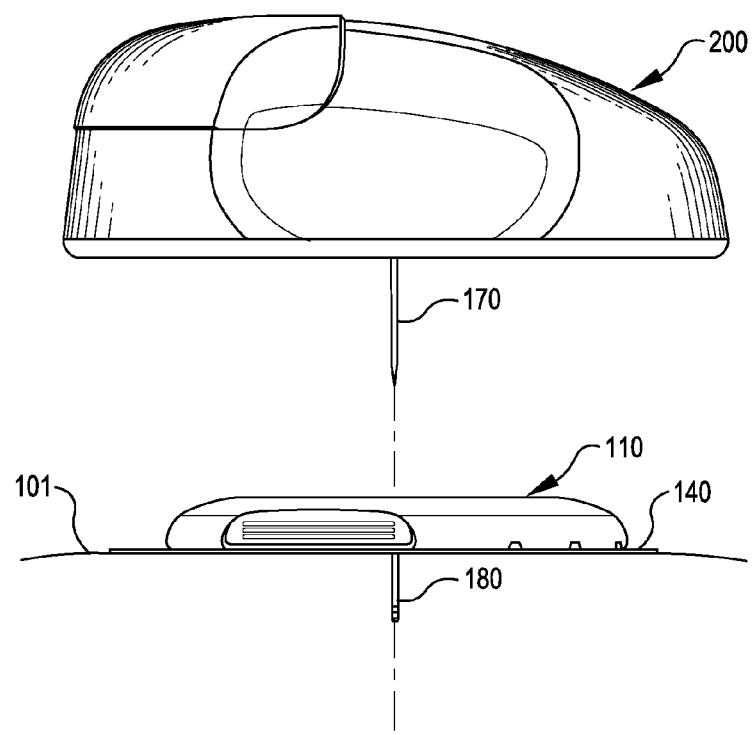
FIG. 24 is an exploded plan view illustrating the device deployed on a user's skin with the inserter separated from the device.

FIG. 24 shows the device 110 on the patient's skin 101 after the inserter 200 has been removed. The adhesive layer 140 of the device is adhered to the patient's skin. FIG. 24 also illustrates the inserter 200 and the insertion needle 170 being pulled from the device 110 in the direction of the arrow. The insertion needle 170 is attached to the handle 120 (not shown), which is in turn received in opening 206 (see FIG. 19). Thus, when inserter 200 is pulled upward from device 110, handle 120, and thus needle 170 are pulled also. Alternatively, the needle handle 120 is arranged to separate from the opening 206 when the inserter 200 is pulled upward. Thereafter, the needle handle 120 may be manually pulled from the device 110 by the user.

Figure 25:
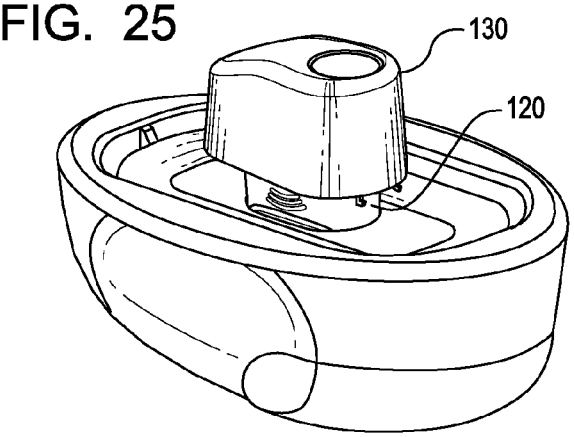
FIG. 25 is a perspective view illustrating the cannula cover being replaced over the inserter needle and needle handle.

As shown in FIG. 25, the cannula cover 130 may now be placed over the needle handle 120. This serves to safely store the needle.

Figure 26:
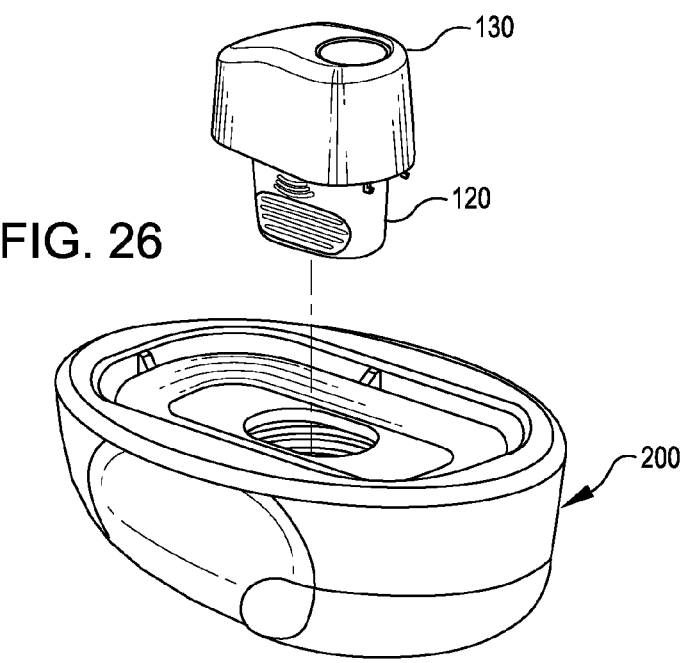
FIG. 26 is an exploded perspective view illustrating the inserter needle cover removed from the inserter and joined into the cannula cover for safely storing the inserter needle and permitting inserter reuse.
Figure 27:
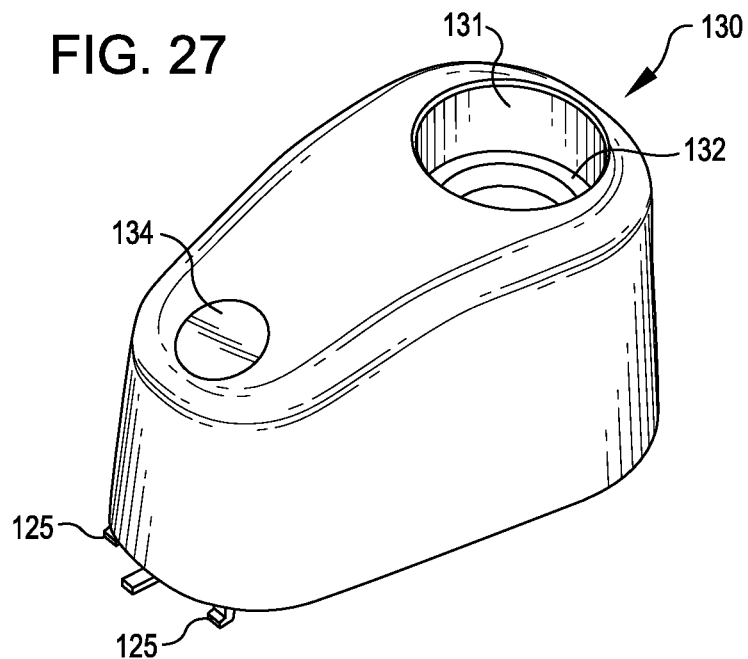
FIG. 27, it is a top perspective view of the cannula cover to illustrate further details in accordance with one embodiment of the present invention.

The needle is now safely stored within cannula cover 130. Further, as may be seen in FIG. 26, the needle handle 120, and the cannula cover 130, and the needle (not shown) safely stored therein may now be removed as a single unit from the inserter 200. This allows the inserter 200 to be reused with another infusion device while still maintaining the safe storage of the insertion needle. Referring now to FIG. 27, it is a top perspective view of the cannula cover 130 to illustrate further details thereof. Here it may be seen that the opening 131 that receives the syringe S (FIG. 5) defines a cylindrical channel that includes an annular shoulder 132 therein. As will be seen subsequently, the annular shoulder 132 forms a stop that limits the depth in which the needle of the syringe may penetrate the device. This prevents accidental damage to the device during filling.

The cannula cover 130 also includes a priming window 134. The window 134 is aligned with the cannula when the device is primed. This enables actual viewing of the cannula tip end during priming. FIG. 27 also shows the feet 125 that permit the cannula cover 130 to be releasably attached to the body of the infusion device as previously described.

Figure 28:
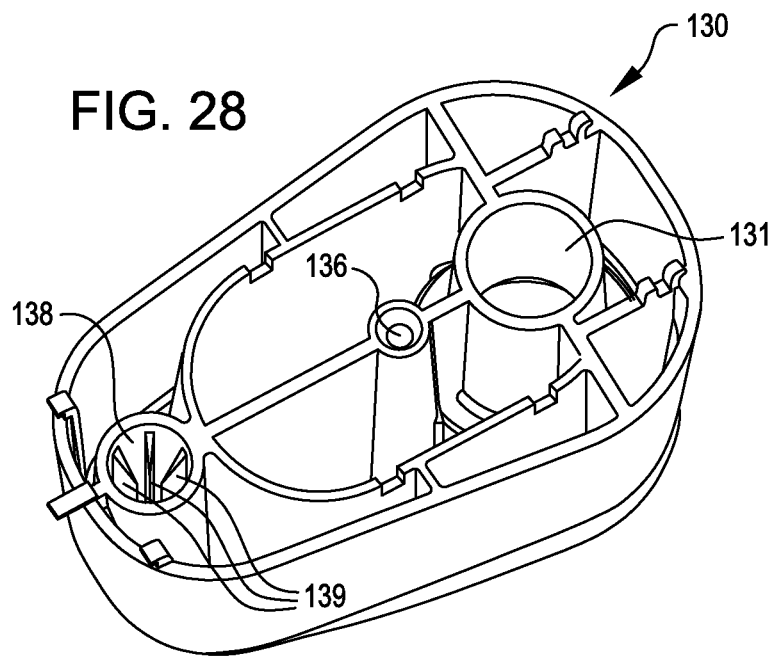
FIG. 28, it is a bottom perspective view of the cannula cover of FIG. 27.

Referring now to FIG. 28, it is a bottom perspective view of the cannula cover 130. In addition to the opening 131, the cannula cover includes the cavity 136 and a priming channel 138.

The cavity 136 is arranged to receive the inserter needle when the handle, with inserter needle, are joined with the cannula cover after the device has been deployed as previously described. This again, provides for the safe storage of the inserter needle within the cavity 136.

The priming channel 138 terminates with the priming window 134 (FIG. 27). The channel 138 has a plurality of radially inwardly projecting and longitudinally extending fins 139. As previously described, when the device is primed, the cannula is covered with the cannula cover 130 and the cannula is carried on the insertion needle. Hence, the cannula and insertion needle extend into the bore 138 during priming. The fins 139 are arranged to be adjacent the distal end of the cannula.

Figure 29:
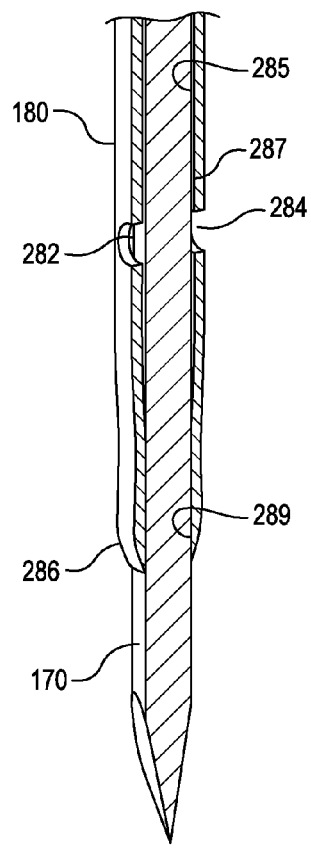
FIG. 29 is a perspective side view, to an enlarged scale and with portions cut away, of a cannula and an insertion needle according to an embodiment of the present invention.

FIG. 29 is a perspective side view, to an enlarged scale and with portions cut away, of a cannula 180 and insertion needle 170 according to further aspects of the present invention. Here it may be seen that the cannula 180 has aligned side ports 282 and 284. The side ports 282 and 284 are directly opposite each other so as to project medicament in opposite directions. The inner channel 285 of the cannula is tapered at its distal end 286 and terminates in a central, tip end, output port 289. The size of the output port 289 is such that it is nearly sealed by the insertion needle 170 while, because of the taper in the inner channel 285, an annular passage 287 to the side ports 282 and 284 is provided. Hence, during priming of the device, the fluid is forced down the annular passage 287. Nearly all of the fluid passing down the passage 287 exits through the side ports 282 and 284. The fluid exiting the side ports 282 and 284 may be viewed through the priming window 134 (FIG. 27) to indicate the device is adequately primed for use.

The fins 139 are arranged to be adjacent the side ports 282 and 284 during priming and present a large surface area to the fluid exiting the side ports. This results in a surface tension that captures the exiting fluid between the fins. Later, when the device is deployed and the cannula cover and insertion needle handle are joined, the fluid that exited the device during priming will be captured therein. The longitudinal extent of the channel 138 and fins 139 enable cannulas and insertion needles of different lengths to be accommodated. Also, the channel 138 serves a dual purpose of protecting the cannula and insertion needle prior to deployment and also facilitating priming of the device.

The side ports 282 and 284 also provide an additional function. During use of the device, should the opening at the distal tip end of the cannula ever become clogged, the medicament will still be administered to the patient through the side ports. Hence the side ports provide an auxiliary medicament delivery path for the device.

Figure 30:
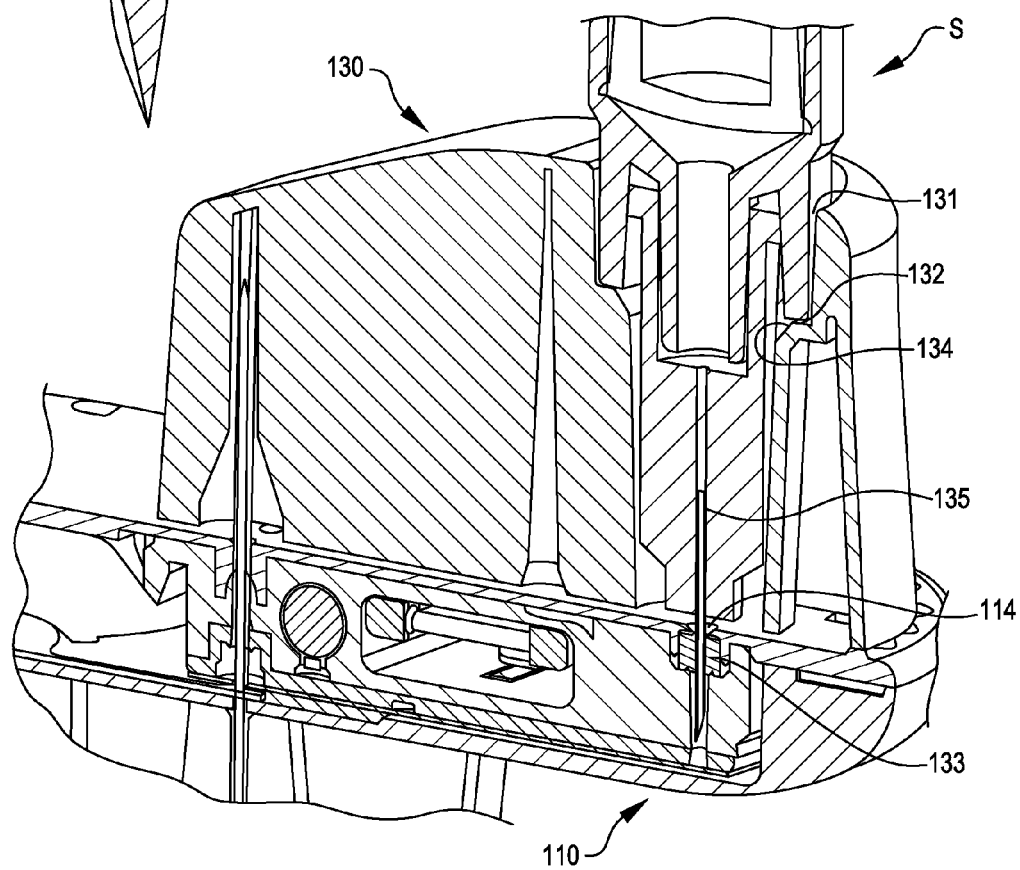
FIG. 30 is a partial sectional side view in perspective showing the syringe in the filling position within the device according to an embodiment of the invention.

Referring now to FIG. 30, it is a partial sectional side view in perspective showing the syringe S in the filling position within the device 110. Here it may be seen that the filling syringe S includes an annular surface 134 that engages the annular shoulder 132 of the filling channel 131. By engaging the annular surface 134 of the syringe S, the annular shoulder 132 forms a stop structure that limits the depth of penetration of the syringe needle 135 within the fill port 114. More specifically, the tip end of the syringe needle 135 is permitted to extend just through the filling septum 133 to protect the device from damage. Hence, the cannula cover opening 131 not only serves to guide the syringe S into the device for filling, but it also protects the device from damage by the needle.

While particular embodiments of the present invention have been shown and described, modifications may be made. It is therefore intended in the appended claims to cover all such changes and modifications which fall within the true spirit and scope of the invention as defined by those claims.

What is claimed is:

1. A drug infusion device comprising:
a housing
a skin-adherable surface forming one surface of the housing;
a reservoir within the housing for holding a medicament;
a cannula extending from the housing and arranged to be deployed beneath the skin of a patient that delivers the medicament to the patient;
an actuator to drive a medicament from the reservoir to the cannula;
an insertion needle port in the housing that receives an insertion needle and which fluidly communicates with the cannula;
a septum configured to seal the insertion port;
a septum pincher configured to press against the septum to assist the septum in sealing the insertion needle port; and
a last-dose lock-out mechanism and an occlusion detection mechanism, wherein both the last-dose lock-out mechanism and the occlusion detection mechanism are configured to operate on the same actuator.

* * * * *